US010006927B2

(12) United States Patent
Sinz et al.

(10) Patent No.: US 10,006,927 B2
(45) Date of Patent: Jun. 26, 2018

(54) METHOD OF OPERATING A LABORATORY AUTOMATION SYSTEM AND A LABORATORY AUTOMATION SYSTEM

(71) Applicant: Roche Diagnostics Operations, Inc., Indianapolis, IN (US)

(72) Inventors: Achim Sinz, Waiblingen (DE); Namitha Mallikarjunaiah, Kornwestheim (DE); Christoph Pedain, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 115 days.

(21) Appl. No.: 15/153,888

(22) Filed: May 13, 2016

(65) Prior Publication Data

US 2016/0341750 A1 Nov. 24, 2016

(30) Foreign Application Priority Data

May 22, 2015 (EP) .................................... 15168782

(51) Int. Cl.
 *G01N 35/00* (2006.01)
 *G01N 35/02* (2006.01)
 (Continued)

(52) U.S. Cl.
 CPC ....... *G01N 35/0092* (2013.01); *G01N 35/026* (2013.01); *G01N 35/04* (2013.01);
 (Continued)

(58) Field of Classification Search
 CPC ... G01N 2035/0401; G01N 2035/0406; G01N 2035/0462; G01N 2035/0477;
 (Continued)

(56) References Cited

U.S. PATENT DOCUMENTS 3,273,727 A 9/1966 Rogers et al.
3,653,485 A 4/1972 Donlon
(Continued)

FOREIGN PATENT DOCUMENTS

CN 201045617 Y 4/2008
CN 102109530 A 6/2011
(Continued)

*Primary Examiner* — Jennifer Wecker
(74) *Attorney, Agent, or Firm* — Roche Diagnostics Operations, Inc.

(57) ABSTRACT

A method of operating a laboratory automation system is presented. The laboratory automation system comprises a plurality of laboratory stations and a plurality of sample container carriers. The sample container carriers carry one or more sample containers. The sample containers comprise samples to be analyzed by the laboratory stations. The system also comprises a transport plane. The transport plane supports the sample container carriers. The system also comprises a drive. The drive moves the sample container carriers on the transport plane. The method comprises, during an initialization of the laboratory automation system, logically reserving at least one buffer area on the transport plane and, after the initialization of the laboratory automation system, buffering in the at least one buffer area sample container carriers carrying sample containers comprising samples waiting for a result of an analysis. Depending on the result of the analysis, the samples are further processed.

13 Claims, 6 Drawing Sheets

(51) Int. Cl.
  *G01N 35/04* (2006.01)
  *G01N 1/00* (2006.01)
  *B65G 35/06* (2006.01)
  *B65G 43/00* (2006.01)
  *B65G 1/137* (2006.01)
  *B65G 43/08* (2006.01)

(52) U.S. Cl.
  CPC .............. *B65G 1/137* (2013.01); *B65G 43/08* (2013.01); *G01N 35/00584* (2013.01); *G01N 35/00603* (2013.01); *G01N 2035/0401* (2013.01); *G01N 2035/0406* (2013.01); *G01N 2035/0462* (2013.01); *G01N 2035/0477* (2013.01); *G01N 2035/0491* (2013.01)

(58) Field of Classification Search
  CPC ......... G01N 35/00603; G01N 35/0092; G01N 35/04; G01N 2035/0491; G01N 35/00584; G01N 35/026; B65G 1/137; B65G 43/08
  See application file for complete search history.

(56) References Cited

U.S. PATENT DOCUMENTS

| | | |
|---|---|---|
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grechsch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Talmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 * | 9/2002 | Sakazume .......... G01N 35/0095 422/65 |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,211,543 B2 | 12/2015 | Ohga et al. |
| 9,239,335 B2 | 1/2016 | Heise |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus |
| 2011/0287447 A1 | 11/2011 | Norderhaug |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |

(56) References Cited

U.S. PATENT DOCUMENTS

| | | |
|---|---|---|
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | H01-266860 A | 10/1989 |
| JP | H02-87903 A | 3/1990 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 4/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 3112393 A | 9/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/064656 A1 | 5/2013 |
| WO | 2013/099647 A1 | 7/2013 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

METHOD OF OPERATING A LABORATORY AUTOMATION SYSTEM AND A LABORATORY AUTOMATION SYSTEM

CROSS-REFERENCE TO RELATED APPLICATIONS

This application claims priority to EP 15168782.9, filed May 22, 2015, which is hereby incorporated by reference.

BACKGROUND

The present disclosure relates to a method of operating a laboratory automation system and a laboratory automation system.

Laboratory sample distribution systems can be used to distribute samples between pluralities of laboratory stations in a laboratory automation system. For example, two-dimensional laboratory sample distribution system providing high throughput are known. Electro-magnetic actuators are disposed below a transport plane in order to drive sample container carriers carrying sample containers on the transport plane.

There is a need to provide for a method of operating a laboratory automation system and a laboratory automation system enabling a high sample throughput.

SUMMARY

According to the present disclosure, a laboratory automation system and method are presented. The laboratory automation system can comprise a plurality of laboratory stations and a plurality of sample container carriers. The sample container carriers can be adapted to carry one or more sample containers. The sample containers can comprise samples to be analyzed by the laboratory stations. The system can further comprise a transport plane. The transport plane can be adapted to support the sample container carriers. The system can further comprise a driver. The driver can be adapted to move the sample container carriers on the transport plane. The system can further comprise a control unit. The control unit can be adapted to logically reserve at least one buffer area on the transport plane during an initialization of the laboratory automation system and, after the initialization of the laboratory automation system, to buffer in the at least one buffer area sample container carriers carrying sample containers, where the sample containers comprise samples waiting for a result of an analysis. Depending on the result of the analysis, the samples can be further processed.

Accordingly, it is a feature of the embodiments of the present disclosure to provide for a method of operating a laboratory automation system and a laboratory automation system enabling a high sample throughput. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
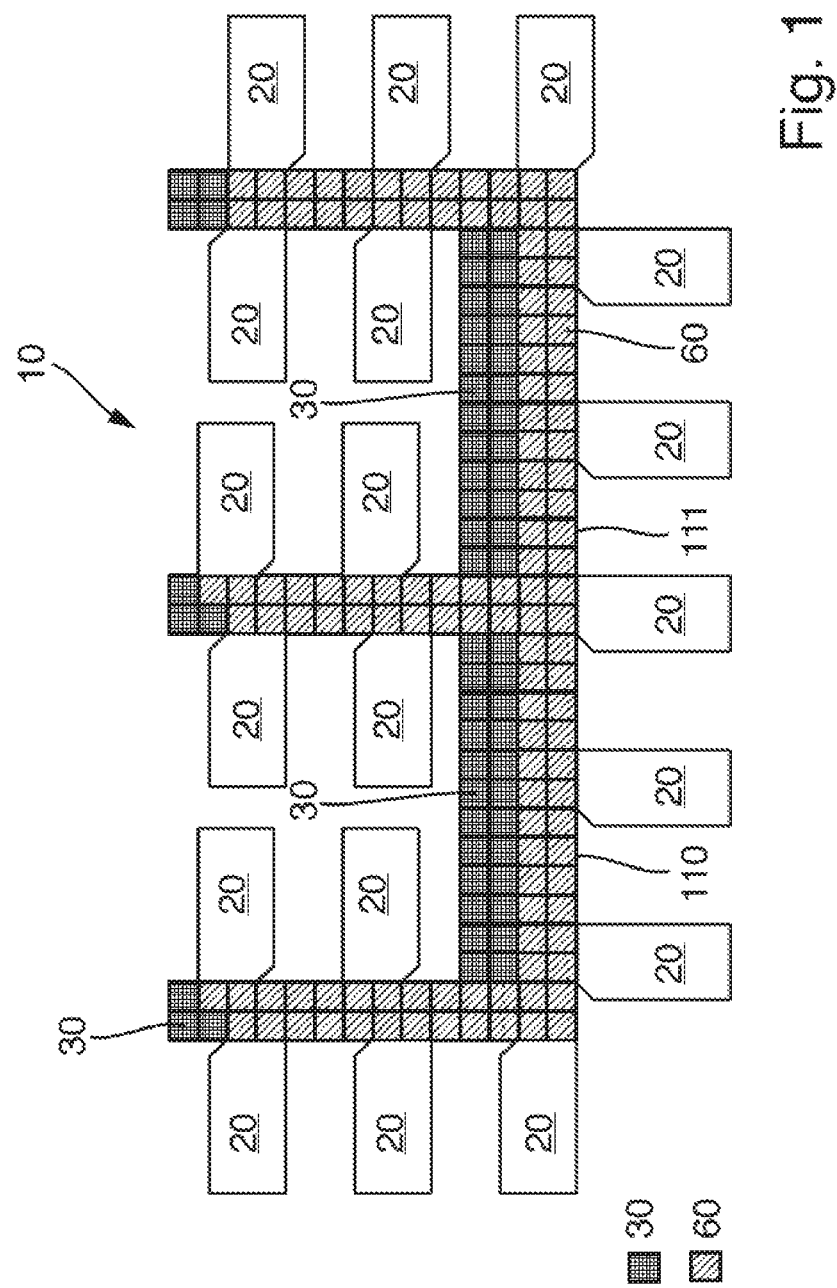
FIG. 1 illustrates schematically a laboratory automation system in a top view in a basic configuration according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method can be adapted to operate a laboratory automation system. The laboratory automation system can comprise a plurality (e.g. 2 to 50) of laboratory stations such as, for example, pre-analytical, analytical and/or post-analytical stations. Pre-analytical stations may be adapted to perform any kind of pre-processing of samples, sample containers and/or sample container carriers. Analytical stations may be adapted to use a sample or part of the sample and a reagent to generate a measuring signal, the measuring signal indicating if and in which concentration, if any, an analyte exists. Post-analytical stations may be adapted to perform any kind of post-processing of samples, sample containers and/or sample container carriers. The pre-analytical, analytical and/or post-analytical stations may comprise at least one of a decapping station, a recapping station, a centrifugation station, an archiving station, a pipetting station, a sorting station, a tube type identification station, and a sample quality determining station.

The laboratory automation system can further comprise a plurality (e.g. 10 to 10000) of sample container carriers. The sample container carriers can be adapted to carry one or more sample containers or sample tubes. The sample containers can comprise, or contain, samples to be processed, especially analyzed, by the laboratory stations. In addition, a plurality of sample containers may exist not containing samples, i.e. empty sample containers, to use, for example, aliquoting.

The laboratory automation system can further comprise a, for example, substantially planar, transport plane. The transport plane can be adapted to support the sample container carriers, i.e. the sample container carriers can be placed on top of the transport plane and can be moved on top of and over the transport plane.

The laboratory automation system can further comprise a drive. The drive can be adapted to move the sample container carriers in two dimensions (x and y) on the transport plane.

The operating method can comprise, during an initialization (for example, starting or booting) of the laboratory automation system, at least one buffer area can be logically reserved on the transport plane, e.g. based on simulation data. In other words, a part of the transport plane can be reserved for one or more buffer areas.

After the initialization of the laboratory sample distribution system and during a normal operational mode, sample container carriers carrying specific sample containers can be buffered inside the at least one reserved buffer area. These specific sample containers can comprise samples that are, at the moment, waiting for a result of an analysis previously started and typically not finished yet. Depending on the result of the analysis, the samples can be further processed, especially further analyzed, or do not have to be further processed, especially do not have to be further analyzed. Additionally, samples waiting for a conditional re-analysis or so called re-run, reflex testing, and the like may be buffered in the at least one reserved buffer area. The buffer area can serve as an efficient cache for the samples (and the corresponding sample container carriers) waiting for a conditional further processing/analyzing. If further processing/analyzing is necessary, the sample container carriers carrying the sample containers comprising the respective samples can be removed from the buffer area and can be transported over the transport plane to the corresponding laboratory station performing the further processing/analyzing. If further processing/analyzing is not necessary, the sample container carrier can be removed from the buffer area and can, for example, be distributed or transported to a post-processing device, which e.g. can safely remove the sample container (and the corresponding sample container carrier, if necessary) from the transport plane.

In the prior art, samples waiting for a conditional further processing/analyzing are typically buffered inside a laboratory station in dedicated so called add-on buffers. For that purpose, dedicated space inside the laboratory station, dedicated devices, and the like have to be provided together with the laboratory station. According to the present disclosure, buffer areas can be dynamically allocated on the transport plane serving as "add-on buffers". Consequently, the laboratory stations do not have to be equipped with dedicated add-on buffers.

After the initialization of the laboratory automation system, operating data of the laboratory automation system can be collected. During a next, or following, initialization of the laboratory automation system, properties of the least one buffer area can be set depending on the collected operating data. This can allow for a dynamic optimization of the buffer area such as, for example, regarding location and/or size of the buffer area, depending on specific operating conditions.

The properties of the least one buffer area can be set depending on a time of day, and/or a volume of traffic (traffic load), and/or a date, and/or a geographical region, and/or defective laboratory stations, and/or disease scenarios. The properties can be chosen from a group comprising: a number of the buffer areas, and/or a location of the at least one buffer area, and/or a shape of the at least one buffer area, and/or a size of the at least one buffer area.

The buffer area replacing the conventional add-on buffer can be specifically tailored depending on current operating conditions of the laboratory automation system. If, for example, typically more samples have to be buffered during s specific time of day, the size of the buffer area may be increased during this specific time of day. In case of a flu epidemic typically requiring specific analyses which can only be provided by a specific laboratory station, a sufficiently large buffer area may be provided close to that laboratory station. If a significant amount of traffic on the transport plane occurs, the buffer area may be minimized and specifically tailored such that sufficient transport space can be available on the transport plane to ensure high traffic volume. The buffer area may replace the conventional add-on buffer completely or partially. The conventional add-on buffer can e.g. still be used for Add-On tests requiring low access time and the inventive buffer area can be used for Add-On tests requiring a very short access time.

The sample container carriers can be entered into the at least one buffer area or removed from the at least one buffer area over (passing) dedicated buffer area interface locations, i.e. the interface locations can serve as a gate (entrance/exit) to the buffer areas. This can reduce the complexity of managing the buffer area. It can be possible, that the at least one buffer area can additionally buffer a number of sample container carriers not carrying a sample container. If, for example, a sample container carrier carrying a sample container is entered into the at least one buffer area, in return a sample container carrier not carrying a sample container can be removed from the at least one buffer area. Accordingly, if a sample container carrier carrying a sample container is removed from the at least one buffer area, in return a sample container carrier not carrying a sample container can be entered into the at least one buffer area.

The transport plane can comprise a number of analyzer interface locations. The analyzer interface locations can be assigned to corresponding laboratory stations. Samples, and/or sample containers, and/or the sample container carriers can be transferred to/from the laboratory stations using the analyzer interface locations. For example, a pick-and-place device can pick a sample container comprised in a sample container carrier located at one of the analyzer interface locations and transfer the sample container to the laboratory station. Accordingly, a sample container can be transferred from one of the laboratory stations to an empty sample container carrier located on the analyzer interface location.

The transport plane can be segmented into logical fields. The at least one buffer area can be logically formed from an integer number (e.g. 2 to 200) of logical fields. The logical fields can, for example, be square shaped and can be of identical size and outline. The logical fields can be arranged in a chess board manner.

The laboratory automation system can comprise a plurality of laboratory stations.

The laboratory automation system can further comprise a plurality of sample container carriers. The sample container carriers can be adapted to carry one or more sample containers. The sample containers can comprise samples to be analyzed by the laboratory stations.

The laboratory automation system can further comprise a transport plane. The transport plane can be adapted to support the sample container carriers.

The laboratory automation system can further comprise a drive. The drive can be adapted to move the sample container carriers on the transport plane.

The laboratory automation system can further comprise a control unit such as, for example, in the form of a microprocessor and program storage. The control unit can be adapted to control the laboratory automation system such that the method as described above can be performed. The control unit can, for example, be adapted to logically reserve at least one buffer area on the transport plane during an initialization of the laboratory automation system. After the initialization of the laboratory automation system, the control unit can be adapted to buffer in the at least one reserved buffer area sample container carriers carrying sample containers, which can be sample containers comprise samples waiting for a result of an analysis. Depending on the result of the analysis, the samples can be further processed, especially further analyzed.

The sample container carriers can comprise at least one magnetically active device such as, for example at least one permanent magnet. The drive can comprise a plurality of electro-magnetic actuators being stationary arranged in rows and columns below the transport plane. The electro-magnetic actuators can be adapted to apply a magnetic drive force to the sample container carriers. The control unit can be adapted to activate the electromagnetic actuators such that the sample container carriers can move simultaneously and independently from one another over the transport plane and enter or leave the at least one buffer area.

The logically reserved buffer areas can be visualized on the transport plane, such that an operator can control the properties of the reserved buffer areas and, if necessary, manually adjust the properties. In order to visualize the buffer areas, visualizing means, for example, in the form of light emitting devices such as LEDs can be arranged below the transport plane. The transport plane can be at least partially translucent. For example, for each electro-magnetic actuator, a corresponding LED may be provided placed adjacent to the electro-magnetic actuator. The visualizing means may further be used to visualize the operating state of the corresponding electro-magnetic actuator and may, for example, indicate if the corresponding electro-magnetic actuator is defective. Additionally, if the transport plane is segmented into a number of separate modules, defective modules may be signalized by the visualizing means located inside the defective module.

Referring initially to FIG. 1, FIG. 1 schematically shows a laboratory automation system 10 in a top view in a basic or initial configuration. The laboratory automation system 10 can comprise a plurality of laboratory stations 20 arranged adjacent to a transport plane 110 having a "UU-shape". The laboratory stations 20 can be distributed as depicted along the outline of the transport plane 110. The transport plane 110 can be adapted to carry a plurality of sample container carriers 140 (see FIG. 5).

Figure 5:
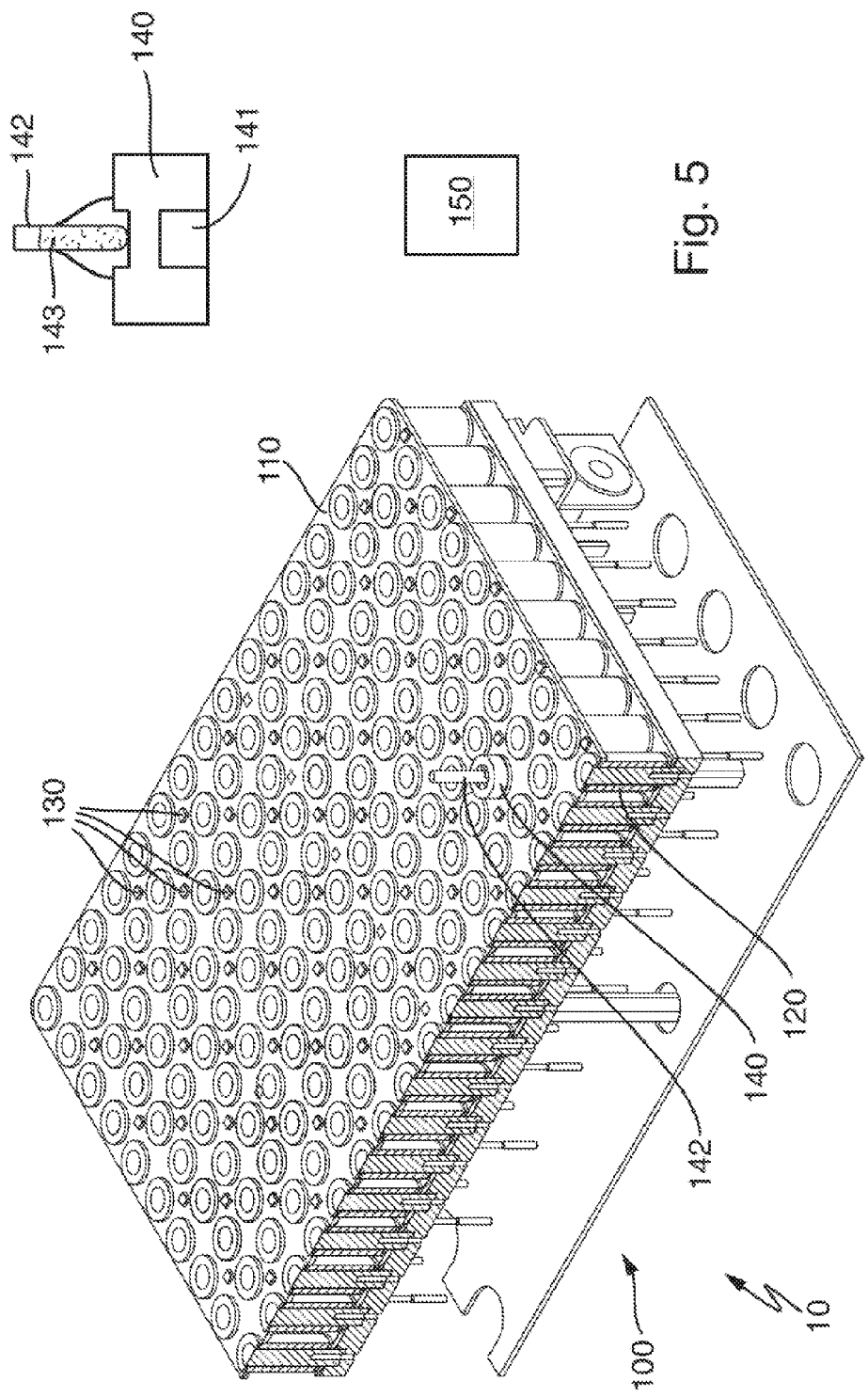
FIG. 5 illustrates shows a drive of the laboratory automation system of FIG. 1 in a perspective view according to an embodiment of the present disclosure.

Referring to FIG. 5 which depicts an exemplary sample container carrier 140, the sample container carriers 140 can each comprise a magnetically active device 141 in the form of a permanent magnet. Although for the sake of explanation only one sample container carrier 140 is depicted, self-evidently typically a large number of sample container carriers 140 can be arranged on the transport plane 110. The sample container carriers 140 can carry sample containers 142 containing a respective sample 143.

Further referring to FIG. 5, a drive 120 in the form of electro-magnetic actuators can be stationary arranged in rows and columns below the transport plane 110. The electro-magnetic actuators 120 can be adapted to apply a magnetic drive force to the sample container carriers 140, such that sample container carriers 140 can be distributed over the transport plane 110 on desired transport paths simultaneously and independent from one another, if necessary.

Hall sensors 130 can be distributed over the transport plane 110. The hall sensors 130 can be adapted to determine the respective positions of the sample container carriers 140 on the transport plane 110.

Now referring back to FIG. 1, the transport plane 110 can be logically segmented into equally-sized, square shaped logical fields 111. Each logical field 111 can be assigned to, i.e. covers, a corresponding electro-magnetic actuator 120 as depicted in FIG. 5.

Further referring to FIG. 5, the laboratory automation system 10 can comprise a control unit 150. The control unit 150 can be adapted to control, or activate, the electromagnetic actuators 120 such that the sample container carriers can move 140 over the transport plane 110.

Further, the control unit 150 can logically reserves buffer areas 30 on the transport plane 110 during an initialization, or boot-up, of the laboratory automation system 10. After the initialization of the laboratory automation system 10, the control unit 150 can control the electromagnetic actuators 120 such that sample container carriers 140 carrying so called add-on samples 143 can be buffered in one of the buffer areas. An add-on sample 143 can be waiting for a result of an analysis actually being performed regarding the add-on sample by one of the laboratory stations 20. Depending on the result of the analysis, the add-on samples 143 can have to be further analyzed or not. The buffer area 30 to be used to buffer the add-on sample may be selected according to a plurality of criteria. Typically, the buffer area 30 closest to the laboratory station 20 performing the analysis can be selected.

The buffer areas can be logically formed from an integer number of logical fields 111. Two of the buffer areas 30 can be formed from three logical fields 11, one buffer area 30 can be formed from four logical fields 111, and two buffer areas 30 can be formed from twenty-four logical fields 111.

In addition to the buffer areas 30, a track area 60 can be logically formed on the transport plane 110. The track area 60 can be used to distribute, or transport, the samples (i.e. the sample container carriers 140 carrying the sample containers 142 containing the sample 143) between the laboratory stations 20.

The properties of the buffer areas 30 and the property of the track area 60 can be set depending on a plurality of criteria as will be explained in detail below.

Figure 2:
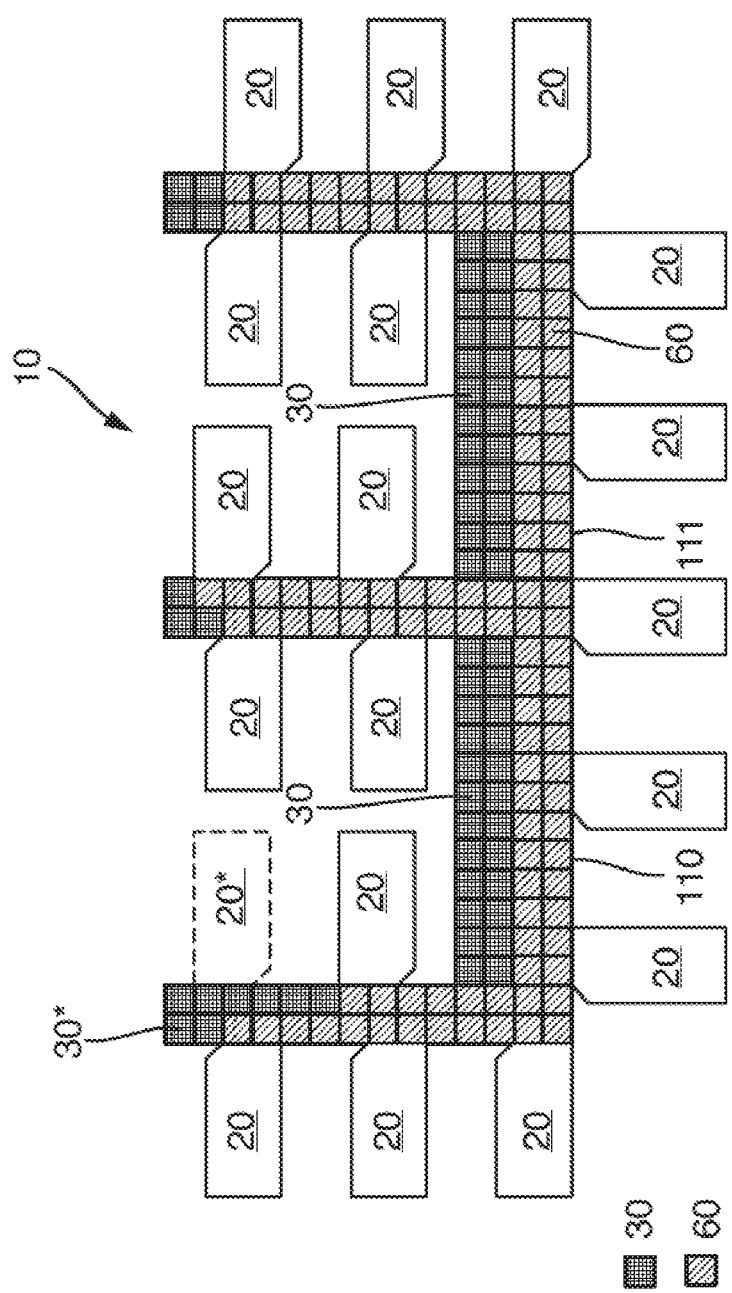
FIG. 2 illustrates schematically the laboratory automation system in a modified configuration in which one of a plurality of laboratory stations of the laboratory automation system is defective according to an embodiment of the present disclosure.

FIG. 2 depicts the laboratory automation system 10 in a top view in a configuration, in which the laboratory station 20* is defective. Since it is not necessary to transport samples to the defective laboratory station 20*, the size and the outline of the buffer area 30* close to the defective laboratory station 20* can be adapted dynamically. The buffer area 30* in FIG. 2 can comprise eight logical fields 111. The corresponding buffer area 30 of FIG. 1 can comprise only three logical fields 111. Further, the outline or shape can be adapted, as depicted in FIG. 2.

When the control unit 150 determines that the laboratory station 20* is defective, the control unit 150 can initiate a next initialization (re-initialization) of the laboratory automation system 10, such that the buffer areas 30 can be re-configured as depicted in FIG. 2. Self-evidently, the track area 60 can change accordingly.

Figure 3:
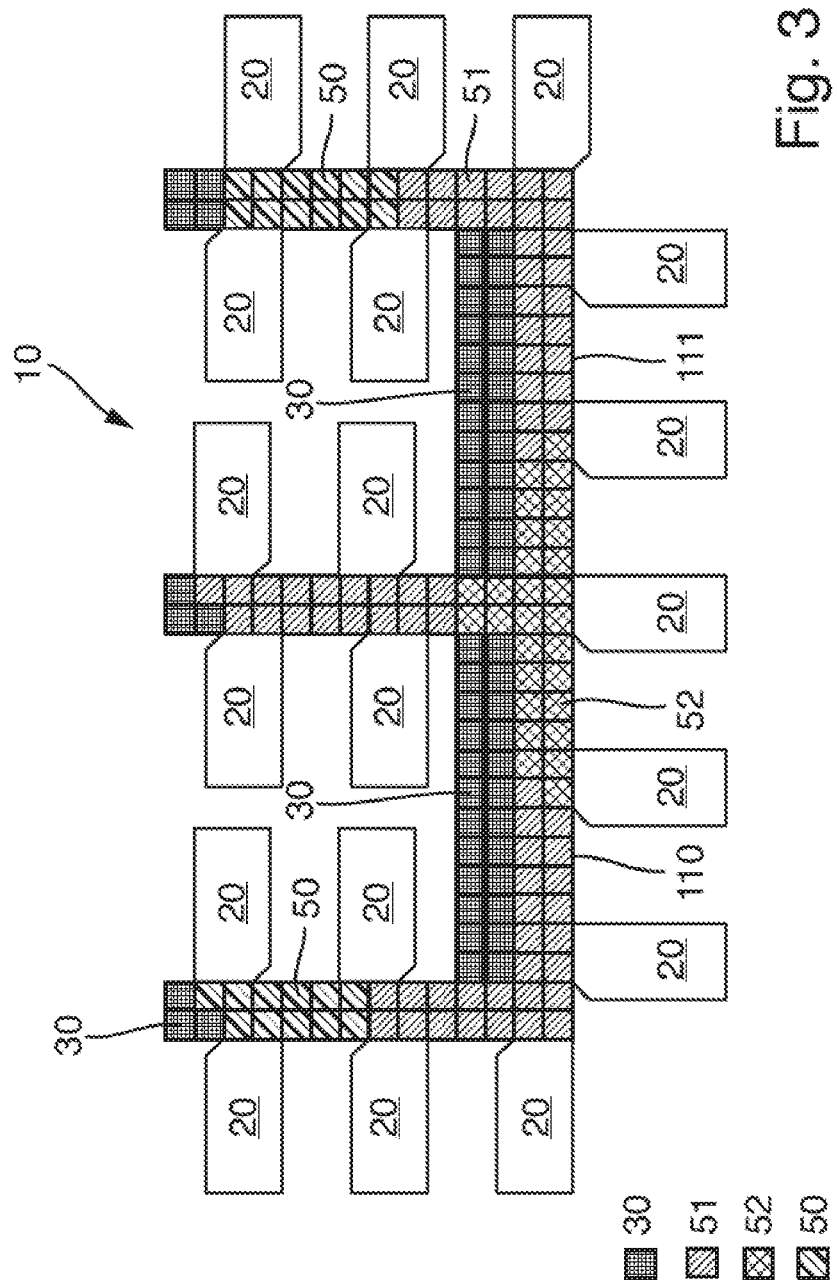
FIG. 3 illustrates schematically traffic loads of the laboratory automation system depicted in FIG. 1 according to an embodiment of the present disclosure.

FIG. 3 schematically shows a volume of traffic on the transport plane 110 based on the configuration depicted in FIG. 1. Three levels of volume of traffic can occur on the transport plane 110. The lowest level of traffic can occur in the area 50, a mid-level of traffic can occur in the area 51, and a high level of traffic can occur in the area 52.

Figure 4:
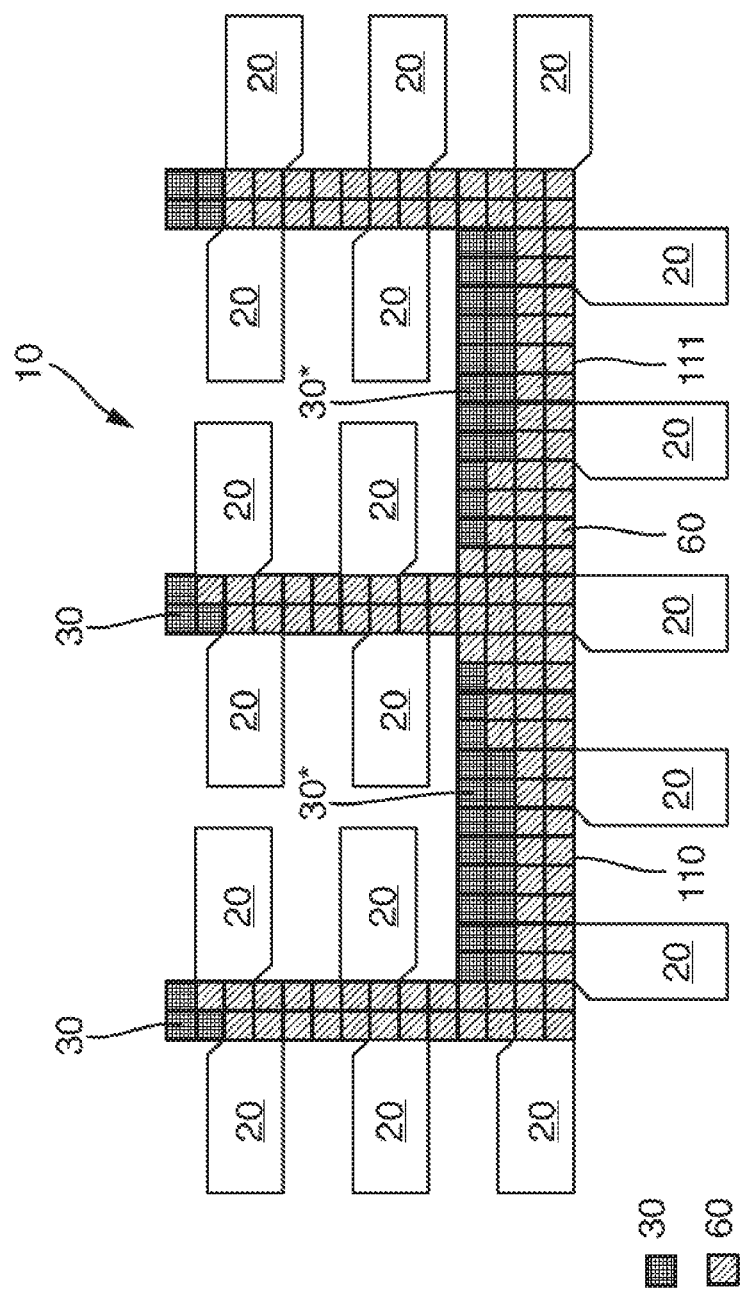
FIG. 4 illustrates schematically the laboratory automation system in a top view in a configuration based on the traffic loads depicted in FIG. 3 according to an embodiment of the present disclosure.

The control unit 150 can collect operating data of the laboratory automation system 10, inter alia in form of the volume of traffic as depicted in FIG. 3. When the control unit 150 determines significant volume of traffic in specific regions on the transport plane 110, the control unit 150 can initiate a next initialization (re-initialization) of the laboratory automation system 10, such that the buffer areas 30 can be re-configured as depicted in FIG. 4. Self-evidently, the track area 60 can change accordingly.

Referring to FIG. 4, the outline and the number of logical fields of the larger buffer areas 30* can be changed compared to FIG. 3, such that in the area of high volume of traffic the buffer size can be reduced to correspondingly increase the track area 60 in the critical region, such that a larger track area can be available in the critical region.

Figure 6:
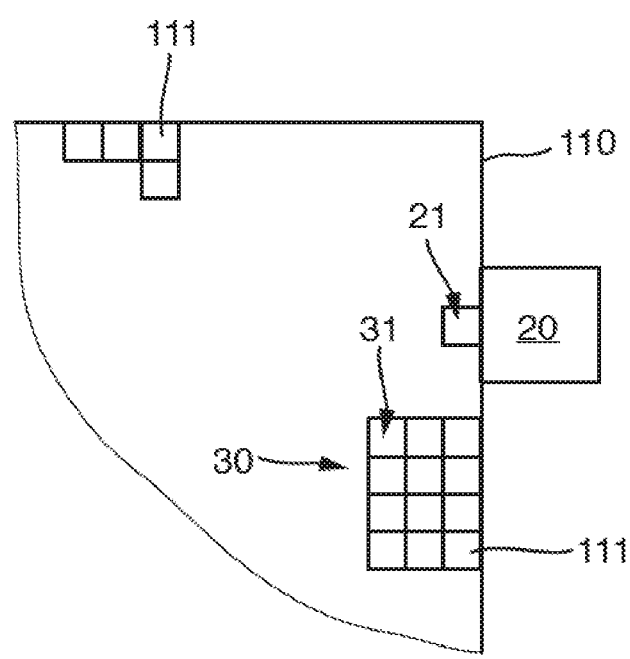
FIG. 6 illustrates schematically an analyzer interface location assigned to a laboratory station and a buffer area having a buffer area interface location according to an embodiment of the present disclosure.

FIG. 6 schematically shows an analyzer interface location 21 assigned to one of the laboratory stations 20. Further, FIG. 6 schematically shows one of the buffer areas 30 having a buffer area interface location 31.

Sample container carriers 140 can be entered into the buffer areas 30 or re-moved from the buffer areas 30 exclusively over the respective buffer area interface locations 31. The buffer areas 30 can comprise one or more than one corresponding interface location 31.

Samples 143, and/or sample containers 142, and/or the sample container carriers 140 can be transferred to/from the respective laboratory stations 20 using the corresponding analyzer interface locations 21. For example, a pick-and-place device can pick a sample container 142 comprised in a sample container carrier 140 located at one of the analyzer interface locations 21 and transfer the sample container 143 to the laboratory station 20. Accordingly, a sample container can be transferred from one of the laboratory stations 20 to an empty sample container carrier 140 located on the analyzer interface location 21.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of operating a laboratory automation system, wherein the laboratory automation system comprises a plurality of laboratory stations, a plurality of sample container carriers, wherein the sample container carriers are configured to carry one or more sample containers, wherein the sample containers comprise samples to be analyzed by the laboratory stations, a transport plane, wherein the transport plane is configured to support the sample container carriers, and a drive, wherein the drive is configured to move the sample container carriers on the transport plane, the method comprises:
   during an initialization of the laboratory automation system, logically reserving at least one buffer area on the transport plane based on simulation data; and
   after the initialization of the laboratory automation system, buffering in the at least one logically reserved buffer area sample container carriers carrying sample containers comprising samples waiting for a result of an analysis, wherein depending on the result of the analysis, the samples are further processed.

2. The method according to claim 1, further comprising, after the initialization of the laboratory automation system, collecting operating data of the laboratory automation system; and
   during a next initialization of the laboratory automation system, setting properties of the least one buffer area depending on the collected operating data.

3. The method according to claim 2, further comprising, during the initialization of the laboratory automation system, setting properties of the least one buffer area depending on a time of day, and/or a date, and/or a volume of traffic, and/or a geographical region, and/or defective laboratory stations, and/or disease scenarios.

4. The method according to claim 2, wherein the properties are chosen from a group comprising: a number of the buffer areas, and/or a location of the at least one buffer area, and/or a shape of the at least one buffer area, and/or a size of the at least one buffer area.

5. The method according to claim 1, wherein sample container carriers are entered into the at least one buffer area or removed from the at least one buffer area over dedicated buffer area interface locations.

6. The method according to claim 1, wherein the transport plane comprises a plurality of analyzer interface locations, wherein the analyzer interface locations are assigned to corresponding laboratory stations.

7. The method according to claim 1, wherein the transport plane is segmented into logical fields, wherein the at least one buffer area is logically formed from an integer number of logical fields.

8. A laboratory automation system, the laboratory automation system comprising:
   a plurality of laboratory stations;
   a plurality of sample container carriers, wherein the sample container carriers are configured to carry one or more sample containers, wherein the sample containers comprise samples to be analyzed by the laboratory stations;
   a transport plane, wherein the transport plane is configured to support the sample container carriers;
   a drive, wherein the drive is configured to move the sample container carriers on the transport plane; and
   a control unit, wherein the control unit is programmed to logically reserve at least one buffer area on the transport plane during an initialization of the laboratory automation system based on simulation data, and, after the initialization of the laboratory automation system, to buffer in the at least one logically reserved buffer area sample container carriers carrying sample containers, where the sample containers comprise samples waiting for a result of an analysis, wherein depending on the result of the analysis, the samples are further processed.

9. The laboratory automation system according to claim 8, wherein the sample container carriers comprise at least one magnetically active device.

10. The laboratory automation system according to claim 9, wherein the at least one magnetically active device is a permanent magnet.

11. The laboratory automation system according to claim 9, wherein the drive comprise a plurality of electro-magnetic actuators stationary arranged in rows and columns below the transport plane.

12. The laboratory automation system according to claim 11, wherein the electro-magnetic actuators are configured to apply a magnetic drive force to the sample container carriers.

13. The laboratory automation system according to claim 12, wherein the control unit is programmed to activate the electromagnetic actuators such that the sample container carriers move over the transport plane.

* * * * *